United States Patent
An et al.

(10) Patent No.: US 7,217,815 B2
(45) Date of Patent: May 15, 2007

(54) 2-BETA-MODIFIED-6-SUBSTITUTED ADENOSINE ANALOGS AND THEIR USE AS ANTIVIRAL AGENTS

(75) Inventors: Haoyun An, Carlsbad, CA (US); Yili Ding, Fountain Valley, CA (US); Stephanie Z. Shaw, Rowland Heights, CA (US); Zhi Hong, Aliso Viejo, CA (US)

(73) Assignee: Valeant Pharmaceuticals North America, Aliso Viejo, CA (US)

( * ) Notice: Subject to any disclaimer, the term of this patent is extended or adjusted under 35 U.S.C. 154(b) by 0 days.

(21) Appl. No.: 10/530,627

(22) PCT Filed: Oct. 23, 2002

(86) PCT No.: PCT/US02/34026

§ 371 (c)(1),
(2), (4) Date: Feb. 27, 2006

(87) PCT Pub. No.: WO03/062256

PCT Pub. Date: Jul. 31, 2003

(65) Prior Publication Data

US 2006/0183706 A1  Aug. 17, 2006

Related U.S. Application Data

(60) Provisional application No. 60/350,296, filed on Jan. 17, 2002.

(51) Int. Cl.
*C07H 19/00* (2006.01)
*C07H 19/02* (2006.01)
*C07H 19/04* (2006.01)
*C07H 19/167* (2006.01)

(52) U.S. Cl. ............... 536/27.62; 536/26.1; 536/26.11; 536/26.12; 536/26.13; 536/27.1; 536/27.13; 536/27.2; 536/27.21; 536/27.3; 536/27.6

(58) Field of Classification Search ............... 536/26.1, 536/27.1, 27.13, 27.2, 27.21, 27.3, 27.6, 536/27.62

See application file for complete search history.

(56) References Cited

U.S. PATENT DOCUMENTS

| | | | | |
|---|---|---|---|---|
| 3,480,613 A | * | 11/1969 | Walton | 536/27.23 |
| 6,812,219 B2 | * | 11/2004 | LaColla et al. | 514/49 |
| 2004/0063658 A1 | * | 4/2004 | Roberts et al. | 514/45 |
| 2006/0135465 A1 | * | 6/2006 | An et al. | 514/46 |

FOREIGN PATENT DOCUMENTS

| WO | WO 01/90121 | 11/2001 |
|---|---|---|
| WO | WO 01/92282 | 12/2001 |
| WO | WO 02/18404 | 3/2002 |

* cited by examiner

*Primary Examiner*—Shaojia Anna Jiang
*Assistant Examiner*—Traviss McIntosh
(74) *Attorney, Agent, or Firm*—Thelen Reid Brown Raysman & Steiner LLP

(57) ABSTRACT

Various 2'-beta-methyl-6-substituted adenosine analogs (including 2,6-disubstituted adenosine, 8-aza-6-substituted adenosine, and 2-aza-6-substituted adenosine) are prepared by conventional and combinatorial library approaches. Contemplated compounds are particularly useful as therapeutic agents, and especially as antiviral agents.

5 Claims, No Drawings

2-BETA-MODIFIED-6-SUBSTITUTED ADENOSINE ANALOGS AND THEIR USE AS ANTIVIRAL AGENTS

This application claims the benefit of U.S. provisional patent application with the Ser. No. 60/350,296, filed Jan. 17, 2002, which is incorporated by reference herein.

FIELD OF THE INVENTION

The field of the invention is nucleoside related compounds and their uses, especially for the treatment of viral infections with HCV, HRV, RSV, HIV, HRV as well as viruses in the families of Flaviviridae, Paramyxoviridae, Orthomyxoviridae, Picornaviridae, Bunyaviridae, Arenaviridae, and Herpesviridae.

BACKGROUND OF THE INVENTION

Nucleosides, and especially purine-type nucleosides and their analogs interact with many biological targets, and some nucleoside analogues have been used as antimetabolites for treatment of cancers and viral infections. After entry into the cell, many nucleoside analogues can be phosphorylated to monophosphates by nucleoside kinases, and then further phosphorylated by nucleoside monophosphate kinases and nucleoside diphosphate kinases to give nucleoside triphosphates. Once a nucleoside analogue is converted to its triphosphate inside the cell, it can be incorporated into DNA or RNA. Incorporation of certain unnatural nucleoside analogues into nucleic acid replicates or transcripts can interrupt gene expression by early chain termination or by interfering with the function of the modified nucleic acids. In addition, certain nucleoside analogue triphosphates are very potent, competitive inhibitors of DNA or RNA polymerases, which can significantly reduce the rate at which the natural nucleoside can be incorporated. Many anti-HIV nucleoside analogues fall into this category, including 3'-C-azido-3'-deoxythymidine, 2',3'-dideoxycytidine, 2',3'-dideoxyinosine, and 2',3'-didehydro-2',3'-dideoxythymidine.

Various purine-type and other nucleoside analogues can also act in other ways, for example, causing apoptosis of cancer cells and/or modulating immune systems. In addition to nucleoside antimetabolites, a number of nucleoside analogues that show very potent anticancer and antiviral activities act through still other mechanisms. Some well-known nucleoside anticancer drugs are thymidylate synthase inhibitors such as 5-fluorouridine, and adenosine deaminase inhibitors such as 2-chloroadenosine. A well-studied anticancer compound, neplanocin A, is an inhibitor of S-adenosylhomocysteine hydrolase, which shows potent anticancer and antiviral activities.

Unfortunately, many nucleoside analogues that can inhibit tumor growth or viral infections are also toxic to normal mammalian cells, primarily because these nucleoside analogues lack adequate selectivity between the normal cells and the virus-infected host cells or cancer cells. For this reason many otherwise promising nucleoside analogues fail to become therapeutics in treatment of various diseases.

Selective inhibition of cancer cells or host cells infected by viruses has been an important subject for some time, and tremendous efforts have been made to search for more selective nucleoside analogues. In general, however, a large pool of nucleoside analogues is thought to be necessary in order to identify highly selective nucleoside analogues. Unfortunately, the classical method of synthesizing nucleosides and nucleotides having desired physiochemical properties, and then screening them individually, takes a significant amount of time to identify a lead molecule. Although thousands of nucleoside analogues were synthesized over the past decades, if both sugar and base modifications are considered, many additional analogues are still waiting to be synthesized.

During the last few years, combinatorial chemistry has been used to generate huge numbers of organic compounds other than nucleosides, nucleotides, and their analogs resulting in large compound libraries. If nucleosides, nucleotides, and their analogs could be made through a combinatorial chemistry approach, a large number of such compounds could be synthesized within months instead of decades, and large libraries could be developed. A combinatorial chemistry approach to nucleosides may also encourage a focus beyond previously addressed biological targets. For example, in the past nucleoside analogues were usually designed as potential inhibitors of DNA or RNA polymerases and several other enzymes and receptors, including inosine monophosphate dehydrogenase, protein kinases, and adenosine receptors. If a vast number of diversified nucleoside analogues could be created their use may extend far beyond these previously recognized biological targets, which would open a new era for the use of nucleoside analogues as human therapeutics.

The generation of combinatorial libraries of chemical compounds other than nucleosides, nucleotides, and their analogs by employing solid phase synthesis is well known in the art. For example, Geysen, et al. (*Proc. Natl. Acac. Sci. USA*, 3998 (1984)) describes the construction of a multi-amino acid peptide library; Houghton, et al. (*Nature*, 354, 84 (1991)) describes the generation and use of synthetic peptide combinatorial libraries for basic research and drug discovery, and Lam, et al. (*Nature*, 354, 82 (1991)) describes a method of synthesis of linear peptides on a solid support such as polystyrene or polyacrylamide resin. Although a combinatorial chemistry approach has been proven to work well with many types of compounds, there are numerous problems with the generation of nucleoside libraries. Among numerous other difficulties, most nucleoside analogues contain a sugar moiety and a nucleoside base, which are linked together through a glycosidic bond. The formation of the glycosidic bond can be achieved through a few types of condensation reactions. However, most of the reactions do not give a good yield of desired products, which may not be suitable to the generation of nucleoside libraries.

Moreover, the glycosidic bonds in many nucleosides are in labile to acidic condition, and many useful reactions in combinatorial chemistry approaches cannot be used in the generation of nucleoside analogue libraries. As a result, many researchers focused their attention to areas in pharmaceutical chemistry that appear to present an easier access to potential therapeutic molecules, and there seems to be a lack of methods for generating libraries of nucleosides and nucleotides using solid phase synthesis. Therefore, there is still a need to provide new nucleoside compounds and methods for generation of nucleoside and nucleotide libraries.

SUMMARY OF THE INVENTION

The present invention is directed to nucleoside analog libraries, library compounds, and their methods of use. Particularly contemplated nucleoside analog libraries will include library compounds with a modified sugar portion (most preferably modified at the C2'-position) and a modified heterocyclic adenosine base portion.

In one aspect of the inventive subject matter, contemplated compounds have a structure according to Formula 1 or Formula 2, wherein the substituents X, X', Y, Z, and Z' are as shown in the section entitled "Contemplated Compounds" below.

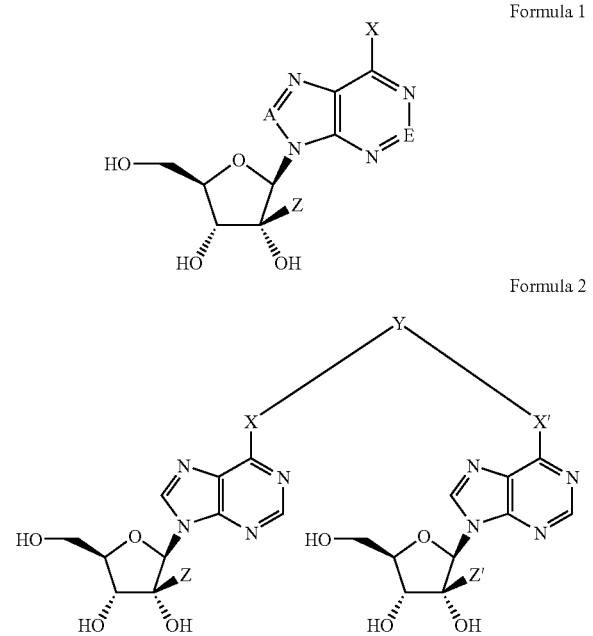

Formula 1

Formula 2

Further contemplated compounds also include prodrugs and metabolites of the above compounds, and in especially preferred aspects, such compounds may include a moiety (e.g., a cyclic phosphate, a cyclic phosphonate, a cyclic phosphoamidate, or a non-cyclic phosphate (di-) ester) that is covalently coupled to the C2'-atom, C3'-atom, and/or C5'-atom (thereby replacing the corresponding OH group), wherein at least part of the moiety is preferentially cleaved from the compound in a target cell or target organ. Especially preferred moieties will have a structure according to Formula M1 or M2, wherein A, B, B', V, W, W', and Z are defined as in the section entitled "Contemplated Compounds" below.

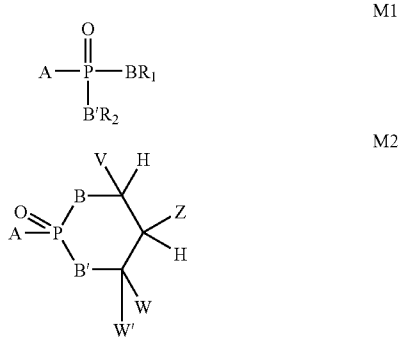

M1

M2

In another aspect of the inventive subject matter, a pharmaceutical composition includes contemplated compounds at a concentration effective to reduce viral propagation of a virus in a patient infected with the virus (e.g., HCV virus, an HRV virus, an RSV virus, an HIV virus, and an HBV virus).

Contemplated compositions may further comprise a second pharmacologically active molecule, and particularly preferred molecules include interferon, and fragments thereof.

Consequently, the inventors contemplate a method of treating a viral infection in a patient in which contemplated compounds are administered to the patient in an amount effective to reduce viral propagation. Viewed from another perspective, the inventors contemplate a method of reducing viral propagation in a cell infected with a virus, wherein contemplated compounds are presenting the cell in an amount effective to reduce viral propagation.

Various objects, features, aspects and advantages of the present invention will become more apparent from the following detailed description of preferred embodiments of the invention.

DETAILED DESCRIPTION

The inventors have discovered that various nucleoside analogs, and especially various 2'-modified 6-substituted adenosine nucleoside analogs may be employed as therapeutic molecules, and especially as antiviral agents (e.g., against HCV).

The term "nucleoside library" as used herein refers to a plurality of chemically distinct nucleosides, nucleotides, nucleoside analogs, and/or nucleotide analogs wherein at least some of the nucleosides, nucleotides, nucleoside analogs, and/or nucleotide analogs include, or have been synthesized from a common precursor.

For example, a plurality of nucleosides, nucleotides, nucleoside analogs, and/or nucleotide analogs that were prepared from a protected ribofuranose as a building block/precursor is considered a nucleoside library under the scope of this definition. Therefore, the term "common precursor" may encompass a starting material in a first step in a synthesis as well as a synthesis intermediate (i.e., a compound derived from a starting material). In another example, at least one step in the synthesis of one of the nucleosides, nucleotides, nucleoside analogs, and/or nucleotide analogs is concurrent with at least one step in the synthesis of another one of the nucleosides, nucleotides, nucleoside analogs, and/or nucleotide analogs, and synthesis is preferably at least partially automated. In contrast, a collection of individually synthesized nucleosides, nucleotides, nucleoside analogs, and/or nucleotide analogs, and especially a collection of compounds not obtained from a nucleoside library, is not considered a nucleoside library because such nucleosides, nucleotides, nucleoside analogs, and/or nucleotide analogs will not have a common precursor, and because such nucleosides, nucleotides, nucleoside analogs, and/or nucleotide analogs are not concurrently produced.

It is further generally contemplated that the complexity of contemplated libraries is at least 20 distinct nucleosides, nucleotide, nucleoside analogs, and/or nucleotide analogs, more typically at least 100 distinct nucleosides, nucleotide, nucleoside analogs, and/or nucleotide analogs, and most typically at least 1000 distinct nucleosides, nucleotide, nucleoside analogs, and/or nucleotide analogs. Consequently, a typical format of a nucleoside library will include multi-well plates, or a plurality of small volume (i.e., less than 1 ml) vessels coupled to each other. The term "library compound" as used herein refers to a nucleoside, nucleotide, nucleoside analog, and/or nucleotide analog within a nucleoside library.

The term "nucleoside" refers to all compounds in which a heterocyclic base is covalently coupled to a sugar, and an especially preferred coupling of the nucleoside to the sugar includes a C1'-(glycosidic) bond of a carbon atom in a sugar to a carbon or heteroatom (typically nitrogen) in the heterocyclic base. The term "nucleoside analog" as used herein refers to all nucleosides in which the sugar is not a ribofuranose and/or in which the heterocyclic base is not a naturally occurring base (e.g., A, G, C, T, I, etc.). It should further be particularly appreciated that the terms nucleoside and nucleoside analog also include all prodrug forms of a nucleoside or nucleoside analog, wherein the prodrug form may be activated/converted to the active drug/nucleoside in one or more than one step, and wherein the activation/conversion of the prodrug into the active drug/nucleoside may occur intracellularly or extracellularly (in a single step or multiple steps). Especially contemplated prodrug forms include those that confer a particular specificity towards a diseased or infected cell or organ, and exemplary contemplated prodrug forms are described in "Prodrugs" by Kenneth B. Sloan (Marcel Dekker; ISBN: 0824786297), "Design of Prodrugs" by Hans Bundgaard (ASIN: 044480675X), or in copending U.S. application Ser. No. 09/594,410, filed Jun. 16, 2000, all of which are incorporated by reference herein.

Similarly, the term "nucleotide" as used herein refers to a nucleoside that is coupled to a 5'-phosphate group (or modified phosphate group, including phosphonate, thiophosphate, phosphate ester, etc.). Consequently, the term "nucleotide analog" refers to a nucleoside analog that is coupled to a 5'-phosphate group (or modified phosphate group, including phosphonate, thiophosphate, phosphate ester, etc.).

As used herein, the terms "heterocycle" and "heterocyclic base" are used interchangeably herein and refer to any compound in which a plurality of atoms form a ring via a plurality of covalent bonds, wherein the ring includes at least one atom other than a carbon atom. Particularly contemplated heterocyclic bases include 5- and 6-membered rings with nitrogen, sulfur, or oxygen as the non-carbon atom (e.g., imidazole, pyrrole, triazole, dihydropyrimidine). Further contemplated heterocylces may be fused (i.e., covalently bound) to another ring or heterocycle, and are thus termed "fused heterocycle" as used herein. Especially contemplated fused heterocycles include a 5-membered ring fused to a 6-membered ring (e.g., purine, pyrrolo[2,3-d]pyrimidine), and a 6-membered ring fused to another 6-membered or higher ring (e.g., pyrido[4,5-d]pyrimidine, benzodiazepine).

Still further contemplated heterocyclic bases may be aromatic, or may include one or more double or triple bonds. Moreover, contemplated heterocyclic bases may further include one or more substituents other than hydrogen, and especially contemplated substituents include those referenced below. Contemplated heterocycles or substituted heterocycles are typically attached directly to nucleoside bases or sugars, but coupling of the heterocyclic base to the sugar may also include a linker moiety with at least 1–4 atoms between the heterocyclic base and the sugar.

As further used herein, the term "sugar" refers to all carbohydrates and derivatives thereof, wherein particularly contemplated derivatives include deletion, substitution or addition of a chemical group in the sugar. For example, especially contemplated deletions include 2'-deoxy and/or 3'-deoxy sugars. Especially contemplated substitutions include replacement of the ring-oxygen with sulfur, methylene, or nitrogen, or replacement of, a hydroxyl group with a halogen, an amino-, sulfhydryl-, or methyl group, and especially contemplated additions include methylene phosphonate groups. Further contemplated sugars also include sugar analogs (i.e., not naturally occurring sugars), and particularly carbocyclic ring systems. The term "carbocyclic ring system" as used herein refers to any molecule in which a plurality of carbon atoms form a ring, and in especially contemplated carbocyclic ring systems the ring is formed from 3, 4, 5, or 6 carbon atoms. Examples of these and further preferred sugars are given below.

The terms "alkyl" and "unsubstituted alkyl" are used interchangeably herein and refer to any linear, branched, or cyclic hydrocarbon in which all carbon-carbon bonds are single bonds. The term "substituted alkyl" as used herein refers to any alkyl that further comprises a functional group, and particularly contemplated functional groups include nucleophilic (e.g., —$NH_2$, —OH, —SH, —NC, etc.) and electrophilic groups (e.g., C(O)OR, C(X)OH, etc.), polar groups (e.g., —OH), non-polar groups (e.g., aryl, alkyl, alkenyl, alkynyl, etc.), ionic groups (e.g., —$NH_3^+$), and halogens (e.g., —F, —Cl), and all chemically reasonable combinations thereof. The terms "alkenyl" and "unsubstituted alkenyl" are used interchangeably herein and refer to any linear, branched, or cyclic alkyl with at least one carbon-carbon double bond. The term "substituted alkenyl" as used herein refers to any alkenyl that further comprises a functional group, and particularly contemplated functional groups include those discussed above.

Furthermore, the terms "alkynyl" and "unsubstituted alkynyl" are used interchangeably herein and refer to any linear, branched, or cyclic alkyl or alkenyl with at least one carbon-carbon triple bond. The term "substituted alkynyl" as used herein refers to any alkynyl that further comprises a functional group, and particularly contemplated functional groups include those discussed above. The terms "aryl" and "unsubstituted aryl" are used interchangeably herein and refer to any aromatic cyclic, alkenyl, or alkynyl. The term "substituted aryl" as used herein refers to any aryl that further comprises a functional group, and particularly contemplated functional groups include those discussed above. The term "alkaryl" is employed where the aryl is further covalently bound to an alkyl, alkenyl, or alkynyl.

Thus, the term "substituted" as used herein also refers to a replacement of a chemical group or substituent (typically H or OH) with a functional group, and particularly contemplated functional groups include nucleophilic (e.g., —$NH_2$, —OH, —SH, —NC, etc.) and electrophilic groups (e.g., C(O)OR, C(X)OH, etc.), polar groups (e.g., —OH), non-polar groups (e.g., aryl, alkyl, alkenyl, alkynyl, etc.), ionic groups (e.g., —$NH_3^+$), and halogens (e.g., —F, —Cl), and all chemically reasonable combinations thereof.

Contemplated Nucleosides

The present invention is generally directed to various heterocyclic nucleoside libraries and library compounds within these libraries, wherein contemplated compounds may be synthesized by medicinal and combinatorial approaches using solution and/or solid phase strategies.

In one aspect of the inventive subject matter, contemplated compounds, libraries, and library compounds will have a structure according to Formula A

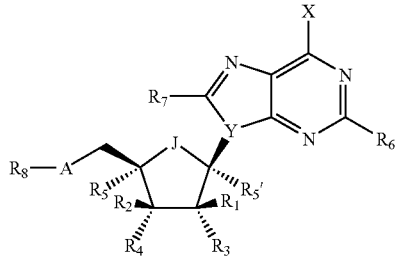

Formula A wherein A is O, CH$_2$, CF$_2$, CCl$_2$, S, NH, or NR; J is O, S, NH, NR, CH$_2$, CH=CH$_2$, or CHR; R$_1$ and R$_2$ are independently H, OH, CH$_3$, CH$_2$CH$_3$, CH(CH$_3$)$_2$, CH$_2$(CH$_2$)$_{2-5}$CH$_3$, C$_1$–C$_8$-alkyl, alkenyl, alkynyl (all of which may be linear, branched, or cyclic), C$_5$–C$_{12}$ aromatic ring or C$_5$–C$_{12}$ heterocyclic ring, halogen (i.e., F, Cl, Br, I), CF$_3$, CHF$_2$, CCl$_3$, CHCl$_2$, CH$_2$Cl, CH$_2$OH, CN, CH$_2$CN, CH$_2$NH$_2$, CH$_2$NHR, CH$_2$OR, CHO, CH$_2$COR, N$_3$, or NH$_2$; R$_3$ and R$_4$ are independently H, OH, OCH$_3$, SH, NH$_2$, NHR, OR, SR, CH$_2$OH, N$_3$, NH$_2$, COOH, halogen, or P(O)(OR)$_2$; R$_5$ and R$_5'$ are independently H, NH$_2$, hydrazino, alkyl, alkenyl, alkynyl, aryl, or heterocycle; R$_6$ and R$_7$ are independently H, NH$_2$, NHR, NHCOR, NRR', NHSO$_2$R, NHCONHR, NHCSNHR, CH$_2$NHR, CHRNHR', NHNH$_2$, CN, alkyl, amino alkyl, alkenyl, alkynyl, CH$_2$-aryl/heterocycles, halogen, OH, or SH; X=H, OH, SH, CN, SR, OR, SNH$_2$, SNHR, C(=NH)NH$_2$, C(=NH)NHOH, NRNR'R, NROR', ONRR' (alternative and/or additional substituents see below); Y is N, CR, or CH; R$_8$ is H, RCO, H$_2$NCH(R)—CO, O$_2$P(O)—O—P(O)O$_2$—O—P(O)O, O$_2$P(O)—O—P(O)O, O$_2$P(O), ester, amide, sulfonate, sulfonamide, halogen, ether, amino, alkylamino, amino acid, phosphodiester, phosphonate ester, phosphoramidate, phosphonamidate, phosphorothioate, cyclic phosphate, cyclic phosphonate, 3',5'-cyclic phosphate/phosphonate; wherein R is a substituted or unsubstituted alkyl, substituted or unsubstituted alkenyl, substituted or unsubstituted alkynyl, substituted or unsubstituted aryl, or substituted or unsubstituted heterocycle; and where R and R' are H, substituted and unsubstituted alkyl, alkenyl, alkynyl, aromatic, heterocyclic groups.

Further contemplated substituents for radical X in Formula A (and Formulae 1 and 2 below) also include the following:

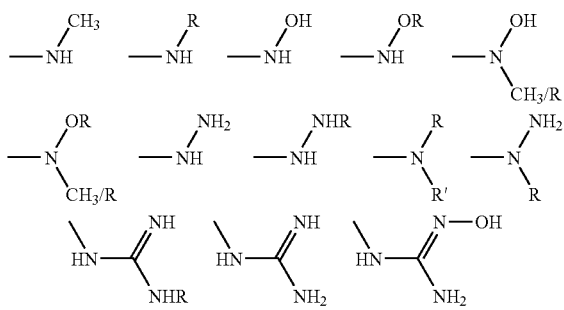

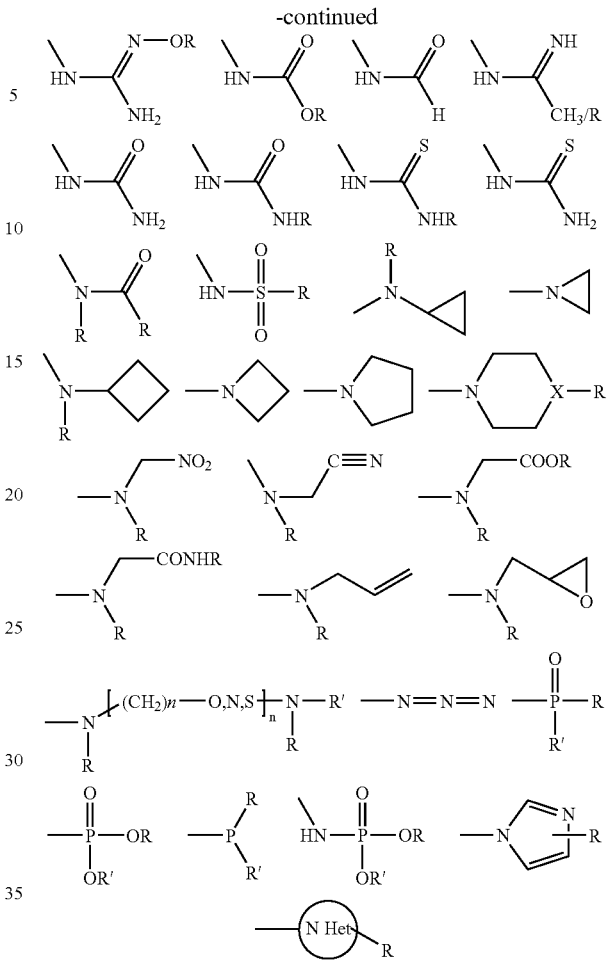

R = C$_1$–C$_8$-alkyl/alkenyl/alkynyl, C$_4$–C$_{12}$-aryl/heterocycles, CF$_3$, CHF$_2$, CCl$_3$, CHCl$_2$, CH$_2$Cl, CH$_2$OH, CH$_2$OR, CN, CH$_2$CN, CH$_2$NH$_2$, CH$_2$NHR, CHO, CH$_2$COR, CONH$_2$, CONHR, C(=NH)NHR, C(=NOH)NHR etc.

6-Substituents: X = NRR', NHOR, NROR, ONRR', ONHCOR, ONHSO$_2$R, ONHCOOR, NRNRR', NHNHCOR, NHNHCOOR, NCORNRR', NHNHCH$_2$CF$_3$, NHNHCH$_2$CH(OH)CH$_2$CH$_2$CH$_3$, NHNHCOCF$_3$, NHNHCH$_2$CH$_2$CH$_3$, NH—N-pophorine, N(Me)NHMe, NHCH$_2$CH$_2$OCH$_3$, NH(CH$_2$)$_{3-5}$OH, NH(CH$_2$)$_{2-4}$OCH$_3$, NHCH$_2$CH$_2$SH, NHCH$_2$CH$_2$SCH$_3$, NHCH$_2$CH$_2$F, NHCH$_2$CF$_3$, NHCH$_2$CH(OH)CH$_2$OH, NHCH$_2$CH(OH)CH$_2$NH$_2$, NHCH(CH$_2$OH)$_2$, N(Me)CH$_2$CH$_2$NHMe, NH(CH$_2$)$_{3-5}$NH$_2$, ONHCOPh, ONEt$_2$, ONHCOCH$_3$, O—N-piperidine, ON(CF$_3$)$_2$, O—N-(C$_4$H$_8$)-cyclic, ONMe$_2$, NMeOH, NHOMe, NHOCH$_2$Ph, NHOCH$_2$CH$_3$ and SCH$_3$, NH$_2$, NHCH$_3$, N(CH$_3$)$_2$, heterocycles,

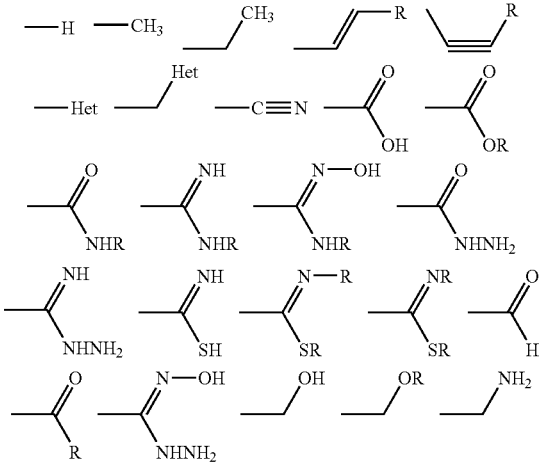

-continued

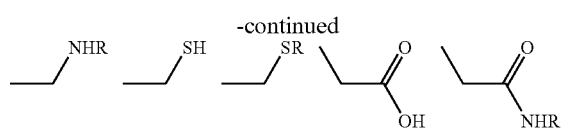

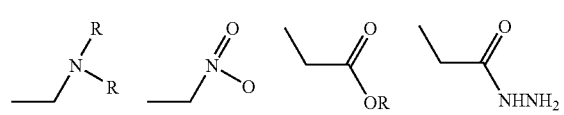

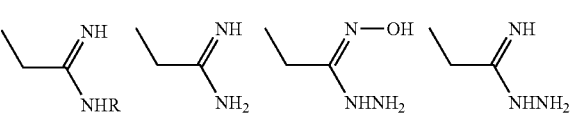

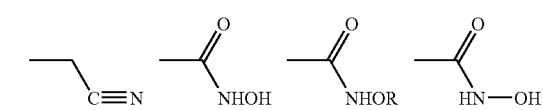

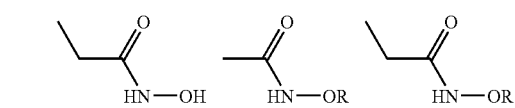

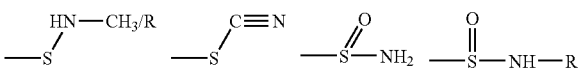

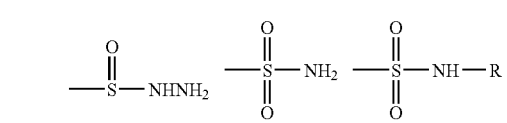

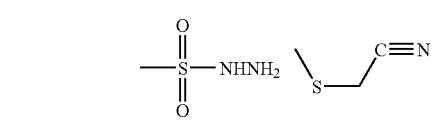

F, Cl, Br, I, SH, SR,

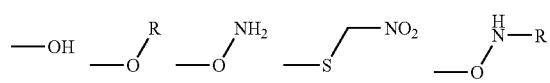

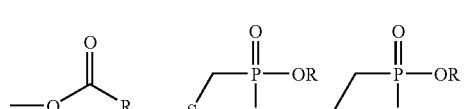

R = $C_1$–$C_8$-alkyl/alkenyl/alkynyl, $C_4$–$C_{12}$-aryl/heterocycles, $CF_3$, $CHF_2$, $CCl_3$, $CHCl_2$, $CH_2Cl$, $CH_2OH$, $CH_2OR$, CN, $CH_2CN$, $CH_2NH_2$, $CH_2NHR$, CHO, $CH_2COR$, $CONH_2$, CONHR, C(=NH)NHR, C(=NOH)NHR etc.

In another aspect of the inventive subject matter, contemplated compounds, libraries, and library compounds will have a structure according to Formula B:

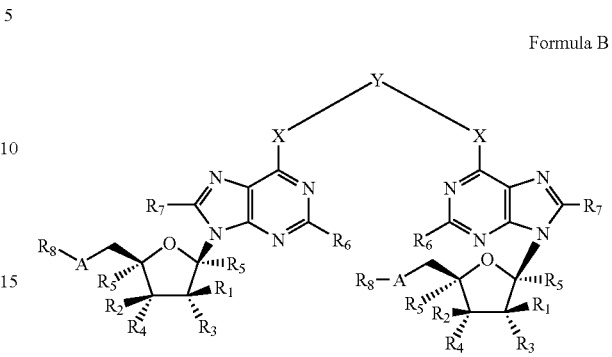

Formula B wherein Y is $(CH_2)_{1-10}$, $(CH_2CH_2O)_{1-3}$, $(CH_2CH_2S)_{1-3}$, a heterocyclic ring, or an aromatic ring; X is O, S, NRNR', $CH_2$, NRO, ONR, $NHSO_2$, C(=NH)NH, C(=NH)NHOH, NRNRR', NROR', or ONRR'; and all other substituents are as defined in Formula A above.

In one particularly preferred aspect of the inventive subject matter, contemplated compounds (which may or may not be derived from a combinatorial library) will have a general structure according to Formula 1:

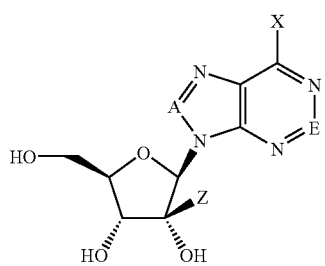

Formula 1 in which Z is an alkyl, an O-alkyl, an alkenyl an alkynyl, or CN, wherein the alkyl, the alkenyl, or the alkynyl may optionally be substituted with a halogen or OH; A is CH or N, and E is C—$R_6$ or N, such that (1) when A is CH then E is C—$R_6$ or N, and (2) when A is N then E is CH; X is $NR_1R_2$, $NR_2NR_3R_4$, $NR_2N=NR_3$, $NR_2N=CHR_3$, $NR_2N=O$, $NR_2C(=O)NR_3R_4$, $NR_2C(=S)NR_3R_4$, $NR_2C(=NH)NR_3R_4$, $NR_2C(=O)NR_2NR_3R_4$, $NR_2OR_3$, ONHC(O)O-alkyl, ONHC(O)O-aryl, $ONR_3R_4$, $SNR_1R_2$, $SONR_1R_2$, or $S(O)_2NR_1R_2$, wherein $R_1$, $R_2$, $R_3$, and $R_4$ are independently H, alkyl, substituted alkyl, cyclic alkyl, heterocyclic alkyl, alkoxy, alkaryl, aryl, heterocyclic aryl, substituted aryl, acyl, substituted acyl, $S(O)_2$-alkyl, NO, $NH_2$, or OH; and wherein $R_6$ is H, $NH_2$, halogen, $N_3$, $NHR_1$, $NHCOR_1$, $NR_1R_2$, $NHSO_2R_1$, $NHCONHR_1$, $NHCSNHR_1$, $CH_2NHR_1$, $CHR_1NHR_2$, $NHNH_2$, CN, alkyl, alkenyl, alkynyl, $CH_2$-aryl, $CH_2$-heterocycle, halogen, OH, or SH. Especially preferred compounds will have an alkyl (and especially $CH_3$) as substituent for the radical Z, A and E are CH, and (I) where X is $NR_1R_2$, it is preferred that $R_1$ is $CH_3$, $NH_2$, or H, and $R_2$ is $CH_2CH_2OH$, $CH_2CH_2NH_2$, $OCH_3$, $CH_3$, or OH, (II) where X is $NHNR_3R_4$, it is preferred that $R_3$ is H, or $CH_3$, and $R_4$ is H, CHO, C(O)$CH_3$, C(O)O$CH_3$, S(O)$_2CH_3$, or $CH_3$, and (III) where X is ONHC(O)O-alkyl or ONHC(O)O-alkaryl, it is preferred that ONHC(O)O-alkyl is ONHC(O)OC(CH$_3$)$_3$ and ONHC(O)O-alkaryl is ONHC(O)O—CH$_2$-phenyl.

In another particularly preferred aspect of the inventive subject matter, contemplated compounds (which may or may not be derived from a combinatorial library) will have a general structure according to Formula 2:

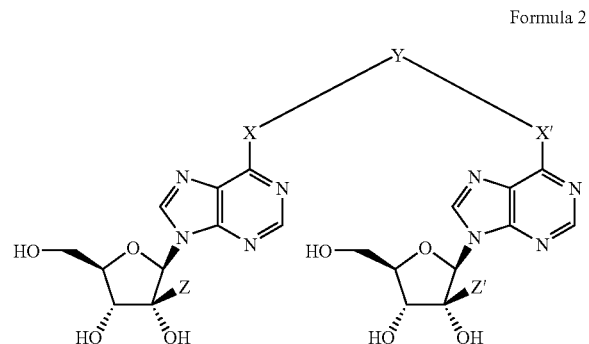

Formula 2 wherein X and X' are independently NH, N-alkyl, or N-substituted alkyl; Y is (CH$_2$)$_{1-10}$, (CH$_2$CH$_2$O)$_{1-3}$, (CH$_2$CH$_2$S)$_{1-3}$, a heterocyclic ring, or an aromatic ring; and Z and Z' are independently selected from the group consisting of an alkyl, an O-alkyl, an alkenyl, an alkynyl, and CN, wherein the alkyl, the alkenyl, or the alkynyl is optionally substituted with a halogen or OH.

Among compounds according to Formula 2, it is especially preferred that at least one of Z and Z' is CH$_3$ and at least one of X and X' is NH. With respect to the connector between the two nucleoside analogs, it is preferred that Y is (CH$_2$)$_{1-10}$ (and most preferably (CH$_2$)$_3$).

It should still further be appreciated that the compounds according to the inventive subject matter also include prodrug forms and/or metabolites. Particularly suitable prodrug forms of contemplated compounds may include a moiety that is covalently coupled to at least one of the C2'-atom, C3'-atom, and C5'-atom, thereby replacing the OH group at the at least one of the C2'-atom, C3'-atom, and C5'-atom, wherein the moiety is preferentially cleaved from the compound in a target cell (e.g., Hepatocyte) or a target organ (e.g., liver). While not limiting to the inventive subject matter, it is preferred that cleavage of the prodrug into the active form of the drug is mediated (at least in part) by a cellular enzyme, particularly receptor, transporter and cytochrome-associated enzyme systems (e.g., CYP-system).

Especially contemplated prodrugs comprise a cyclic phosphate, cyclic phosphonate and/or a cyclic phosphoamidate, which are preferentially cleaved in a hepatocyte to produce the corresponding nucleotides. There are numerous such prodrugs known in the art, and all of those are considered suitable for use herein. However, especially contemplated prodrug forms are disclosed in WO 01/47935 (Novel Bisamidate Phosphonate Prodrugs), WO 01/18013 (Prodrugs For Liver Specific Drug Delivery), WO 00/52015 (Novel Phosphorus-Containing Prodrugs), and WO 99/45016 (Novel Prodrugs For Phosphorus-Containing Compounds), all of which are incorporated by reference herein. Consequently, especially suitable prodrug forms include those targeting a hepatocyte or the liver.

Still further particularly preferred prodrugs include those described by Renze et al. in Nucleosides Nucleotides Nucleic Acids 2001 April–July;20(4–7):931–4, by Balzarini et al. in Mol Pharmacol 2000 November;58(5):928–35, or in U.S. Pat. No. 6,312,662 to Erion et al., U.S. Pat. No. 6,271,212 to Chu et al., U.S. Pat. No. 6,207,648 to Chen et al., U.S. Pat. No. 6,166,089 and U.S. Pat. No. 6,077,837 to Kozak, U.S. Pat. No. 5,728,684 to Chen, and published U.S. Application with the number 20020052345 to Erion, all of which are incorporated by reference herein. Alternative contemplated prodrugs include those comprising a phosphate and/or phosphonate non-cyclic ester (SATE ester, pivaloyl ester, etc.), and an exemplary collection of suitable prodrugs is described in U.S. Pat. No. 6,339,154 to Shepard et al., U.S. Pat. No. 6,352,991 to Zemlicka et al., and U.S. Pat. No. 6,348,587 to Schinazi et al. Still further particularly contemplated prodrug forms are described in FASEB J. 2000 September;14(12):1784–92, Pharm. Res. 1999, August 16:8 1179–1185, and Antimicrob Agents Chemother 2000, March 44:3 477–483, all of which are incorporated by reference herein.

Thus, particularly preferred prodrug forms will comprise a moiety covalently coupled to at least one of the C2'-atom, C3'-atom, and C5'-atom, wherein at least part of the moiety is preferentially cleaved from the compound in a target cell or target organ. As used herein, the term "preferentially cleaved . . . in a target cell or target organ" means that cleavage occurs in a particular target cell or target organ at a rate that is at least 3 times, more typically at least 10 times, and most typically at least 50 times higher than in a non-target cell or non-target organ. The term "target cell" or "target organ" as used herein refers to a cell or organ that is infected with a virus, and especially includes a hepatocyte infected with an HCV virus. Cleavage may be mediated by enzymes (but also by non-enzymatic processes, e.g., via reductive cleavage), and it is particularly preferred that enzymatic cleavage is mediated by a liver-specific enzyme system (e.g., CYP system). Consequently, it should be appreciated that certain prodrug forms of contemplated compounds may be cleaved in a target cell and/or target organ to provide a nucleotide analog. Alternatively, prodrugs may also be converted to the corresponding nucleoside (e.g., where the moiety does not include a phosphorus atom).

An exemplary preferred prodrug of contemplated compounds may therefore include a moiety according to Formula M1 or M2 (covalently coupled to the compound, typically to the C5'-atom, C2'-atom, and/or C3'-atom):

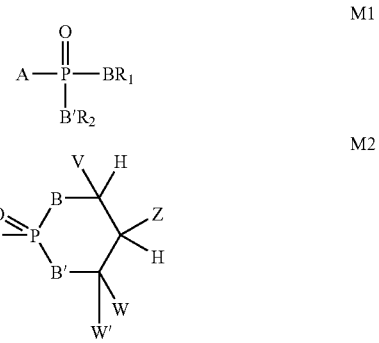

wherein A in M1 or M2 is O or CH$_2$ and replaces the 5'-OH group of the compound of Formula 1 or at least one of the 5'-OH groups of the compound of Formula 2; B and B' are independently O or NH, and where B is NH then R$_1$ or R$_2$ is an amino acid that forms a peptide bond with the N atom of the NH; and R$_1$, R$_2$, V, W, and W' are independently hydrogen, alkyl, alkenyl, alkynyl, aryl, alkaryl, each of which is optionally substituted, and Z is hydrogen, CHWOH, CHWOCOW', SW, or CH$_2$aryl, and where B is O, especially preferred R$_1$ and R$_2$ are CH$_2$CH$_2$SC(=O)t-butyl or CH$_2$C(=O)iPr. Especially preferred compounds according to Formula M2 are those in which A is O or CH$_2$, B and B' are independently O or NH, and in which Z, W, and W' are H and V is m-Chlorophenyl.

With respect to metabolites of contemplated compounds, it should be recognized that all metabolites that have a desirable therapeutic effect, and especially an antiviral effect are deemed suitable. Consequently, particularly suitable metabolites will generally include 5'-phosphates (e.g., monophosphate, diphosphate, and/or triphosphate esters), which may or may not be generated by an enzyme (e.g., kinase, oxidase). Further metabolites include those that are generated via enzymatic action on the heterocyclic base (e.g., via deaminase, deamidase, or hydroxylase).

Exemplary Synthesis of Contemplated C$_2$'-Modified-6-Substituted Purine Nucleosides It should be generally appreciated that contemplated compounds may be synthesized in a variety of procedures. For example, in one exemplary synthetic strategy, C$_2$'-substituted purine nucleoside libraries and compounds may be synthesized as depicted in Scheme 1 below. Here, a suitably C$_2$'-substituted and protected sugar is first coupled to an optionally substituted (e.g., 2- or 8-position) purine heterocyclic base, which is then modified to the desired compound(s) in one or more subsequent reactions.

Scheme 1

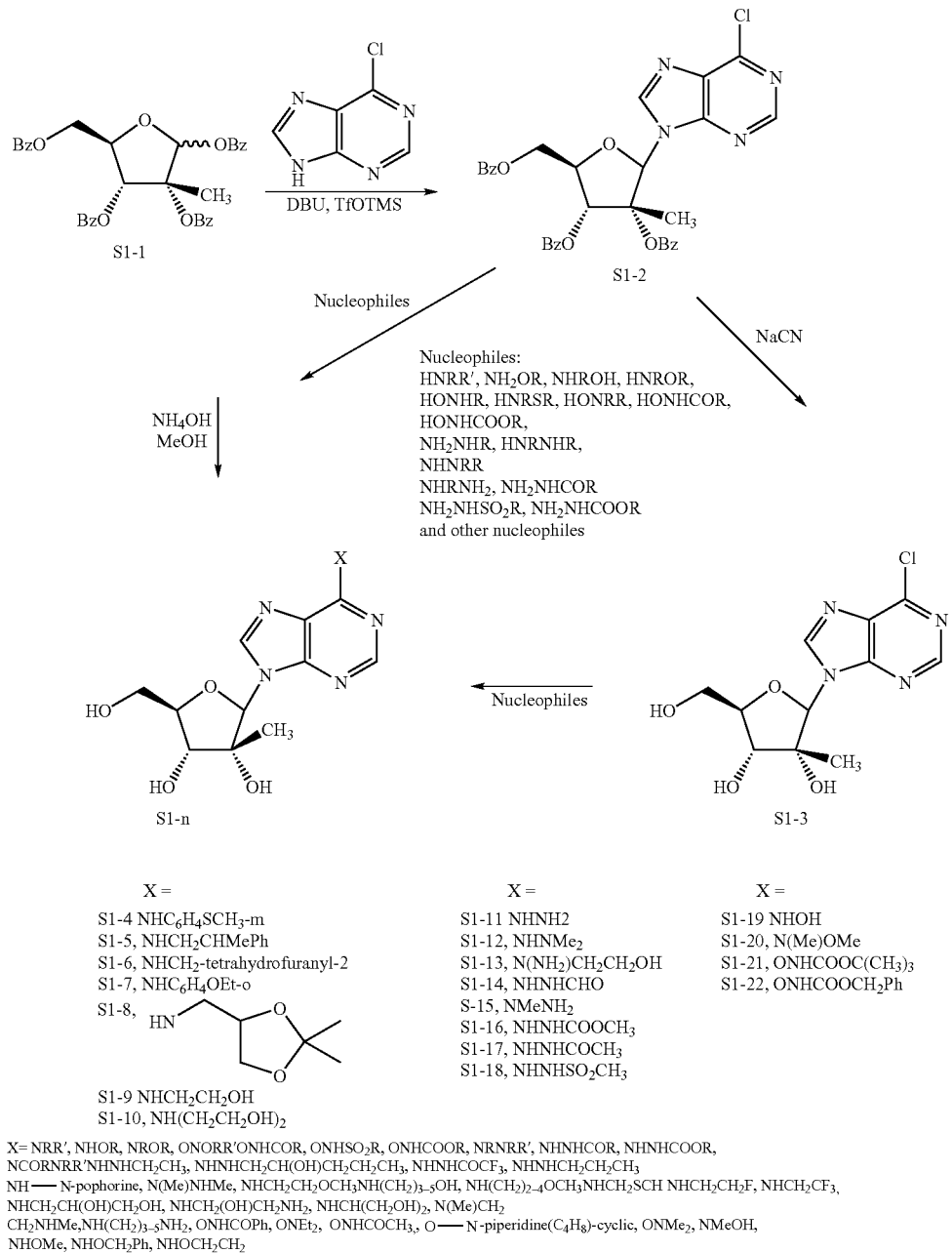

X =
S1-4 NHC$_6$H$_4$SCH$_3$-m
S1-5, NHCH$_2$CHMePh
S1-6, NHCH$_2$-tetrahydrofuranyl-2
S1-7, NHC$_6$H$_4$OEt-o
S1-8,
S1-9 NHCH$_2$CH$_2$OH
S1-10, NH(CH$_2$CH$_2$OH)$_2$ X =
S1-11 NHNH2
S1-12, NHNMe$_2$
S1-13, N(NH$_2$)CH$_2$CH$_2$OH
S1-14, NHNHCHO
S-15, NMeNH$_2$
S1-16, NHNHCOOCH$_3$
S1-17, NHNHCOCH$_3$
S1-18, NHNHSO$_2$CH$_3$ X =
S1-19 NHOH
S1-20, N(Me)OMe
S1-21, ONHCOOC(CH$_3$)$_3$
S1-22, ONHCOOCH$_2$Ph X= NRR', NHOR, NROR, ONORR'ONHCOR, ONHSO$_2$R, ONHCOOR, NRNRR', NHNHCOR, NHNHCOOR, NCORNRR'NHNHCH$_2$CH$_3$, NHNHCH$_2$CH(OH)CH$_2$CH$_2$CH$_3$, NHNHCOCF$_3$, NHNHCH$_2$CH$_2$CH$_3$
NH —— N-pophorine, N(Me)NHMe, NHCH$_2$CH$_2$OCH$_3$NH(CH$_2$)$_{3-5}$OH, NH(CH$_2$)$_{2-4}$OCH$_3$NHCH$_2$SCH NHCH$_2$CH$_2$F, NHCH$_2$CF$_3$,
NHCH$_2$CH(OH)CH$_2$OH, NHCH$_2$(OH)CH$_2$NH$_2$, NHCH(CH$_2$OH)$_2$, N(Me)CH$_2$
CH$_2$NHMe,NH(CH$_2$)$_{3-5}$NH$_2$, ONHCOPh, ONEt$_2$, ONHCOCH$_3$, O —— N-piperidine(C$_4$H$_8$)-cyclic, ONMe$_2$, NMeOH,
NHOMe, NHOCH$_2$Ph, NHOCH$_2$CH$_2$ In especially contemplated aspects, S1-2 of Scheme 1 is reacted with a substituted or unsubstituted amine, or a substituted or unsubstituted hydrazine or other nucleophiles corresponding to the X groups (see e.g., listed above and Scheme 1) to form the corresponding N6-modified adenosine analogs. Particularly preferred amines, hydrazines, and hydroxyamines will have the general formula RNH$_2$, NHRNRR', NHOR', HONRR' wherein R and R' are independently hydrogen, substituted or unsubstituted linear or cyclic alkyl (most preferably between C$_1$ and C$_6$), substituted or unsubstituted alkenyl (most preferably between C$_1$ and C$_6$), substituted or unsubstituted alkynyl (most preferably between C$_1$ and C$_6$), substituted or unsubstituted aryl, thiol, or hydroxyl. For example, suitable amines especially include H$_3$C—NH$_2$, HO—NH$_2$, and H$_2$N—(H$_2$C)$_2$—NH$_2$. However, secondary amines are also contemplated and will generally have the formula RR'NH, with R and R' as defined above.

Consequently, especially preferred compounds will have a structure according to Formulae 3, 4 or 5 as shown below:

Formula 3

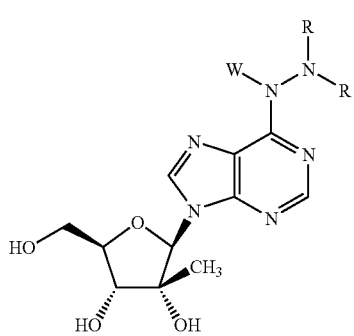

Formula 4

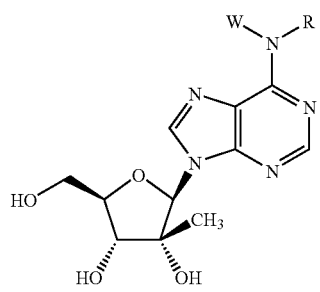

Formula 5

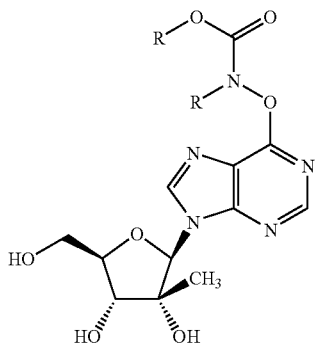

in which W is H, alkyl, alkenyl, alkaryl, aryl, or alkynyl (all of which may be substituted), and most W is preferably CH$_3$, (CH$_2$)$_n$OH with n between 1 and 4, inclusive, N(CH$_3$)(CH$_3$), OH, NHSO$_2$CH$_3$, (CH$_2$)$_n$NH$_2$ with n between 1 and 4, inclusive, or NHCO(O)CH$_3$. R is independently H, substituted or unsubstituted linear or cyclic alkyl, alkenyl, aryl, CH2Ph, or t-butyl. In still further preferred compounds, the C2'-position of suitable sugars may also be modified to a —CH$_2$OH group (in beta orientation).

Still further, and especially where substituted or unsubstituted hydrazines are employed as nucleophilic reagents, dimeric species may be formed as depicted in Scheme 2 below. Particularly preferred hydrazines will have the general formula RNHNH$_2$ or RNR'NH$_2$, wherein R and R' are independently substituted or unsubstituted alkyl linear or cyclic (most preferably between C$_1$ and C$_4$), substituted or unsubstituted alkenyl (most preferably between C$_1$ and C$_4$), substituted or unsubstituted alkynyl (most preferably between C$_1$ and C$_4$), substituted or unsubstituted aryl, hydrogen, thiol, or hydroxyl. For example, suitable amines especially include H$_3$C—NH—NH$_2$, HO—(H$_2$C)$_n$—NH—NH$_2$ when n is between 1–4, inclusive, (H$_3$C)(H$_3$C)N—NH$_2$, H$_3$C—S(O)$_2$—NH—NH$_2$, and H$_3$C—O(O)C—NH—NH$_2$, NH$_2$NH$_2$, NHMeNH$_2$, NH$_2$NHCOCH$_3$.

Scheme 2

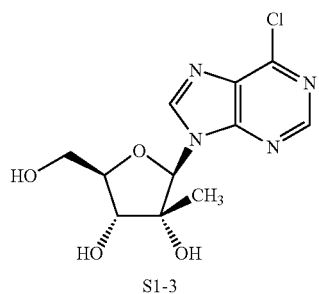

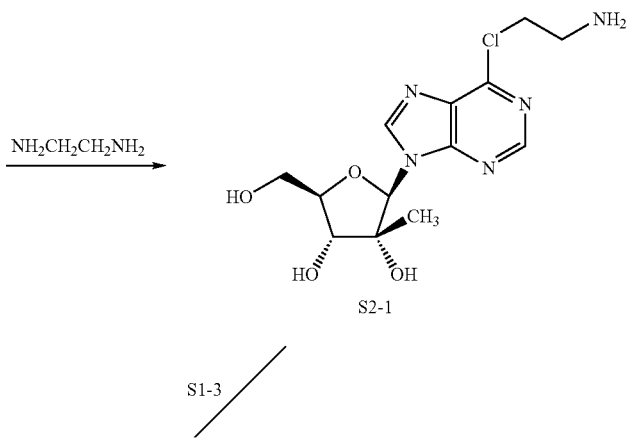

-continued

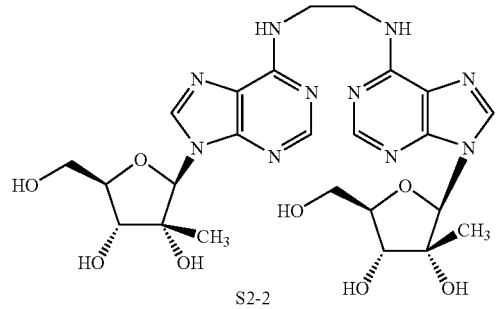

S2-2

In yet further especially preferred aspects of the inventive subject matter, inosine nucleoside analog compounds and libraries may be formed in a process similar to that shown in Scheme 1. In such alternative processes, S1-2 of Scheme 1 is reacted with a substituted or unsubstituted alcohol having a general formula ROH, wherein R is substituted or unsubstituted alkyl (most preferably between $C_1$ and $C_4$), substituted or unsubstituted alkenyl (most preferably between $C_1$ and $C_4$), substituted or unsubstituted alkynyl (most preferably between $C_1$ and $C_4$), substituted or unsubstituted aryl, thiol, ONHC(O)O-aryl or ONHC(O)O-alkyl (alkyl most preferably t-butyl, and aryl most preferably phenyl).

Alternatively, 2'-β-C-alkyl-6-substituted adenosine derivatives may also be synthesized by a solid phase combinatorial approach as depicted in Scheme 3 below. Here, the 2'-β-C-alkyl-6-chloroadenosine S1-2 can be synthesized using a similar route as described above for S1-3 from the corresponding tribenzoyl adenosine derivatives S1-2 with different groups at 2'-β position, which can be synthesized similarly by glycosylation of 6-chloroadenine and the corresponding 2'-β-riboses. Compound S3-1 is then reacted with MMT-Cl polystyrene resin in the presence of pyridine and imidazole to provide the loaded resin S3-2. The resulted resin is then reacted with substituted and unsubstituted amines, hydrazine, hydroxyamine, alcohol, mercapto or other nucleophiles, followed by trifluoroacetic acid cleavage to provide the corresponding 2'-β-alkyl-6-substituted adenosine derivatives S3-3.

Scheme 3

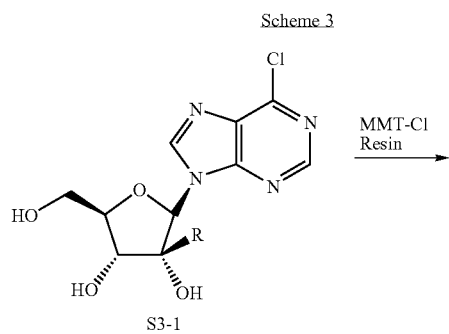

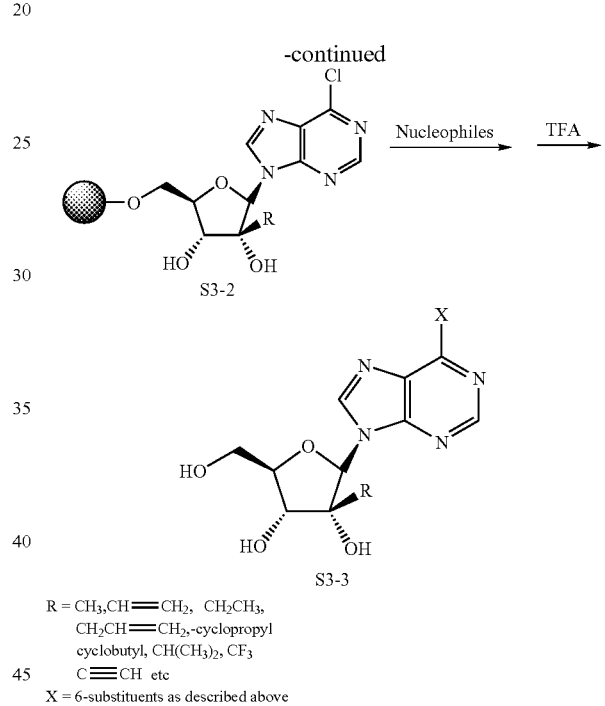

$R = CH_3, CH=CH_2, CH_2CH_3,$
$CH_2CH=CH_2,$-cyclopropyl
cyclobutyl, $CH(CH_3)_2, CF_3$
$C\equiv CH$ etc X = 6-substituents as described above In still further contemplated aspects of the inventive subject matter, it should be recognized that the synthesis of nucleoside analogs may also include coupling of a heterocyclic base other than 6-chloropurine to the sugar moiety, and especially preferred alternative heterocyclic bases include those with an 8-azapurine or 2-azapurine scaffold. Numerous of such alternative heterocyclic bases are commercially available, and where a particular alternative heterocyclic base is not commercially available, it should be appreciated that such bases may readily be synthesized from a commercially available precursor following methods well known to a person of ordinary skill in the art (see e.g., Handbook of Nucleoside Synthesis by Helmut Vorbruggen, Carmen Ruh-Pohlenz, Wiley-Interscience; ISBN: 0471093831).

Consequently, and following procedures substantially identical to those described above, particularly contemplated compounds may be obtained and will have a structure according to Formula 6 (via 2-substituted-6-chloropurine), Formula 7 (via 8-aza-6-chloropurine), or Formula 8 (via 2-aza-6-chloropurine):

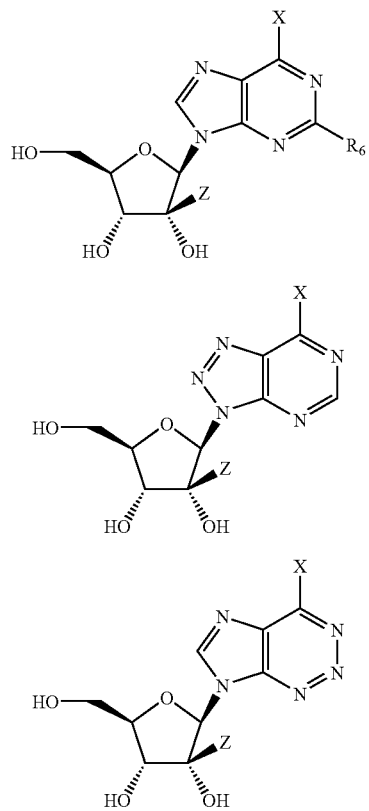

in which the radicals X, Z, and $R_6$ are as defined as in the section entitled "Contemplated Compounds" above.

Use of Contemplated Compounds

It is generally contemplated that contemplated nucleosides have various biological activities, and especially contemplated biological activities include in vitro and in vivo inhibition of DNA and/or RNA polymerases, reverse transcriptases, and ligases. Therefore, contemplated nucleosides will exhibit particular usefulness as in vitro and/or in vivo antiviral agents, antineoplastic agents, or immunomodulatory agents Particularly contemplated antiviral activities include at least partial reduction of viral titers of respiratory syncytial virus (RSV), hepatitis B virus (HBV), hepatitis C virus (HCV), herpes simplex type 1 and 2, herpes genitalis, herpes keratitis, herpes encephalitis, herpes zoster, human immunodeficiency virus (HIV), influenza A virus, Hanta virus (hemorrhagic fever), human papilloma virus (HPV), yellow fever virus, and measles virus.

Especially contemplated immunomodulatory activity includes at least partial reduction of clinical symptoms and signs in arthritis, psoriasis, inflammatory bowel disease, juvenile diabetes, lupus, multiple sclerosis, gout and gouty arthritis, rheumatoid arthritis, rejection of transplantation, giant cell arteritis, allergy and asthma, but also modulation of some portion of a mammal's immune system, and especially modulation of cytokine profiles of Type 1 and Type 2. Where modulation of Type 1 and Type 2 cytokines occurs, it is contemplated that the modulation may include suppression of both Type 1 and Type 2, suppression of Type 1 and stimulation of Type 2, or suppression of Type 2 and stimulation of Type 1.

Therefore, it should be recognized that contemplated compounds may be included in a pharmaceutical composition, wherein contemplated compounds are present at a concentration effective to inhibit viral replication of a virus in a patient infected with the virus, and especially viral replication of the hepatitis C virus. The term "inhibit viral replication" as used herein refers to a reduction in at least one of the initiation of viral nucleic acid synthesis, chain elongation of viral nucleic acid synthesis, processing of viral nucleic acids within a virus infected cell, and viral protein processing/assembly. In alternative aspects of the inventive subject matter, further contemplated viruses that may be treated with contemplated compounds and compositions include HRV virus, RSV virus, HIV virus, HBV virus, and, viruses belonging to the family of Flaviviridae, Paramyxoviridae, Orthomyxoviridae, Picornaviridae, Bunyaviridae, Arenaviridae, and Herpesviridae.

Where contemplated nucleosides are administered in a pharmacological composition, it is contemplated that suitable nucleosides can be formulated in admixture with a pharmaceutically acceptable carrier. For example, contemplated nucleosides can be administered orally as pharmacologically acceptable salts, or intravenously in a physiological saline solution (e.g., buffered to a pH of about 7.2 to 7.5). Conventional buffers such as phosphates, bicarbonates or citrates can be used for this purpose. Of course, one of ordinary skill in the art may modify the formulations within the teachings of the specification to provide numerous formulations for a particular route of administration. In particular, contemplated nucleosides may be modified to render them more soluble in water or other vehicle, which for example, may be easily accomplished with minor modifications (salt formulation, esterification, etc.) that are well within the ordinary skill in the art. It is also well within the ordinary skill of the art to modify the route of administration and dosage regimen of a particular compound in order to manage the pharmacokinetics of the present compounds for maximum beneficial effect in a patient.

In certain pharmaceutical dosage forms, prodrug forms of contemplated nucleosides may be formed for various purposes, including reduction of toxicity, increasing the organ or target cell specificity, etc. Among various prodrug forms, acylated (acetylated or other) derivatives, pyridine esters and various salt forms of the present compounds are preferred. One of ordinary skill in the art will recognize how to readily modify the present compounds to pro-drug forms to facilitate delivery of active compounds to a target site within the host organism or patient. One of ordinary skill in the art will also take advantage of favorable pharmacokinetic parameters of the prodrug forms, where applicable, in delivering the present compounds to a targeted site within the host organism or patient to maximize the intended effect of the compound.

In addition, contemplated compounds may be administered alone or in combination with other agents for the treatment of various diseases or conditions. Combination therapies according to the present invention comprise the administration of at least one compound of the present invention or a functional derivative thereof and at least one other pharmaceutically active ingredient (e.g., antiviral nucleoside drug, interferon or interferon fragment, and particularly interferon alpha). The active ingredient(s) and pharmaceutically active agents may be administered separately or together and when administered separately this may occur simultaneously or separately in any order. The amounts of the active ingredient(s) and pharmaceutically active agent(s) and the relative timings of administration will be selected in order to achieve the desired combined therapeutic effect.

Consequently, a method of treating a viral infection in a patient may comprise a step in which contemplated compounds are administered to a patient in an amount effective to reduce viral propagation. Viewed from another perspective, it is contemplated that a method of reducing viral propagation in a cell infected with a virus may include a step in which the cell is presented with contemplated compounds to the cell in an amount effective to reduce viral propagation according to claim 1, claim 10, claim 12, or claim 17.

Of course it should be recognized that contemplated treatment of a patient and/or contemplated presenting of a cell may also include a step in which the compound is converted in the cell or patient into a metabolite that reduces viral propagation (e.g., where the compound is a nucleoside analog, the conversion may result in the corresponding nucleotide analog. Thus, the metabolite may comprise a phosphate group that is covalently coupled to the C5'-atom via an ester bond with the C5'-OH group).

Experiments and Results

Synthesis of Exemplary Compounds

Compound S1-1 was prepared according to the literature procedure (R. E. Harry O'Kuru, J. M. Smith, M. S. Wolfe, *J. Org. Chem.* 1997, 62, 1754–1759; M. S. Wolfe, R. E. Harry-O'kuru, *Tetrahedron Lett.* 1995, 36, 7611–7614).

6-Chloro-9H-(2'-β-C-methyl-2,3,5-tri-O-benzoyl-β-D-ribofuranosyl)purine (S1-2) was prepared based on the literature procedure (P. Franchetti, L. Cappellacci, S. Marchetti, L. Trincavelli, C. Martini, M. P, Mazzoni, A. Lucacchini, M. Grifantrini, *J. Med. Chem.* 1998, 41, 1708–1715). This compound (40 mg, 0.06 mmol) was treated with methanolic ammonia (15 mL, saturated at 0° C.) and stirred at room temperature for 24 hours in a pressure bottle. The solvent was evaporated to dryness, and the solid residue was purified by silica gel column ($CH_2Cl_2$-MeOH, 10:1) to yield S1-3 as a white solid (8 mg, 44%): $^1$H NMR ($CD_3OD$): δ8.55 (s, 1H), 8.19 (s, 1H), 6.09 (s, 1H), 4.22 (d, 1H, J=9.0 Hz), 4.04 (m, 2H), 3.87 (dd, 1H, J=12.6, 3.0 Hz), 0.89 (s, 3H); $^{13}$C NMR ($CD_3OD$): δ92.0, 83.3, 79.2, 72.9, 59.9. Compound S3-1 were synthesized by the similar procedure from the corresponding 2'-β-alkyl-2',3',5'-tribenzoyl-6-chloroadenosine derivatives.

$N^6$-[3-(Methylthio)phenyl]-9H-(2'-β-C-methyl-β-D-ribofuranosyl)adenine (S1-4). To a solution of 6-chloro-9H-(2'-β-C-methyl-2,3,5-tri-O-benzoyl-β-D-ribofuranosyl)purine (S1-2) (60 mg, 0.09 mmol) in the mixture of ethanol and chloroform (15 ml, 1:1) was treated with 3-(methylthio) aniline (3 equiv). This mixture was stirred at room temperature for 12 hours. The solvent was evaporated, and the residue was treated with methanolic ammonia (15 ml, saturated at 0° C.) in a pressure bottle for 24 hours. The solvent was evaporated to dryness, and the residue was purified by silica gel column ($CH_2Cl_2$-MeOH, 10:1) to yield S1-4 as a yellow oil (20 mg, 55% for two steps): $^1$H NMR ($CD_3OD$): δ8.64 (s, 1H), 8.42 (s, 1H), 7.8 (s, 1H), 7.54 (m, 1H), 7.25 (m, 1H), 6.99 (m, 1H) 4.25 (d, 1H, J=9.0 Hz), 4.04 (m, 2H), 3.89 (dd, 1H, J=12.3, 3.0 Hz), 2.50 (s, 3H), 0.93 (s, 3H); MS: m/z 426 [M+23]$^+$.

$N^6$-(2-Phenylpropyl)-9H-(2'-β-C-methyl-β-D-ribofuranosyl)adenine (S1-5). The title compound was prepared from S1-2 and β-methylphenylethylamine as described for S1-4 (colorless oil, 65% for two steps). $^1$H NMR ($CDCl_3$): δ8.25 (s, 1H), 7.89 (d, 1H), 7.25 (m, 5H), 6.00 (s, 1H), 5.98 (d, 1H), 4.52 (m, 1H), 4.13 (m, 2H), 3.87 (d, 1H), 3.09 (m, 1H), 1.34 (d, 3H), 0.90 (d, 3H).

$N^6$-(R-Tetrahydrofurfuryl)-9H-(2'-β-C-methyl-β-D-ribofuranosyl)adenine (S1-6). The title compound was prepared from S1-2 and R-(−)-tetrahydrofurfurylamine as described for S1-4 (oil, 85% for two steps). $^1$H NMR ($CD_3OD$): δ8.55 (s, 1H), 8.22 (s, 1H), 6.09 (s, 1H), 4.22–3.80 (m, 9H), 2.50–1.69 (m, 21), 0.93 (s, 3H); $^{13}$C NMR ($CDCl_3$): δ92.08, 83.10, 79.16, 77.79, 72.18, 67.91, 59.87, 44.0, 28.58, 25.47, 19.06, 20.6; MS: m/z 366 [M+1]$^+$.

$N^6$-(2-Ethoxybenzyl)-9H-(2'-β-C-methyl-β-D-ribofuranosyl)adenine (S1-7). The title compound was prepared from S1-2 and 2-ethoxybenzylamine as described for S1-4 (colorless oil, 70% for two steps). $^1$H NMR ($CDCl_3$): δ8.40 (s, 1H), 7.90 (s, 1H), 7.30 (m, 3H), 6.82 (m, 3H), 6.60 (s, 1H), 5.95 (s, 1H), 4.80 (s, 2H), 4.45 (s, 1H), 4.10 (m, 6H), 1.42 (s, 3H), 0.92 (s, 3H); $^{13}$C NMR ($CDCl_3$): δ93.9, 89.7, 79.6, 72.2, 63.8, 63.6, 60.6, 21.0, 15.1.

$N^6$-(2,2-Dimethyl-1,3-dioxolane-4-methyl)-9H-(2'-β-C-methyl-β-D-ribofuranosyl)adenine (S1-8). The title compound was prepared from S1-2 and 2,2-dimethyl-1,3-dioxolane-4-methanamine as described for S1-4 (colorless oil, 70% for two steps). $^1$H NMR ($CDCl_3$): δ8.25 (s, 1H), 8.13 (s, 1H), 6.03 (s, 1H), 4.38 (m, 2H), 4.32 (d, 1H, J=8.4 Hz), 4.07 (m, 4H), 3.87 (dd, 1H, J=12.6, 3.0 Hz), 3.73 (m, 1H), 1.42 (s, 3H), 1.32 (s, 3H), 0.89 (s, 3H); $^{13}$C NMR ($CDCl_3$): δ109.8, 93.1, 83.4, 79.6, 79.6, 74.7, 72.4, 67.1, 60.4, 26.9, 25.4, 20.6.

$N^6$-[2-(Hydroxy)ethyl]-9H-(2'-β-C-methyl-β-D-ribofuranosyl)adenine (S1-9). Compound S1-2 (147 mg, 0.24 mmol) was dissolved in a mixture of ethanol (8 mL), chloroform (4 mL) containing hydroxy ethylamine (0.014 mL, 0.24 mmol). The reaction mixture was stirred at room temperature overnight and concentrated. The residue was purified by flash chromatography on silica gel column using $CHCl_3$:MeOH (50:1–10:1) as eluents. The resulted compound was deprotected with NaCN in methanol, and the reaction mixture was worked up and purified by flash chromatography on a silica gel column using $CHCl_3$:MeOH (20:1–2:1) as eluents to afford 11 mg of tan solid (13% overall yield). $^1$H NMR ($CD_3OD$) δ 8.51 (1H, s), 8.23 (1H, s), 6.08 (1H, s), 4.25 (1H, d, J=9.0 Hz), 4.09–4.02 (2H, m), 3.62 (1H, dd, J=2.59, 12.4 Hz), 3.85–3.70 (4H, m), 0.91 (3H, s). MS (EI) m/z 326 (M+1)$^+$. Compound S1-10 was synthesized similarly from 2-(hydroxyethyl)amino ethanol.

6-(Hydrazinyl)-9H-(2'-β-C-methyl-β-D-ribofuranosyl) purine (S1-11). The title compound was prepared from S1-2 and hydrazine as described for S1-4 (colorless oil, 60% for two steps). $^1$H NMR ($D_2O$): δ8.52 (s, 1H), 8.30 (s, 1H), 6.10 (s, 1H), 4.23 (d, 1H, J=9.0 Hz), 4.07 (m, 1H), 4.01 (m, 1H), 3.86 (dd, 1H, J=12.6, 3.3 Hz), 0.91 (s, 3H).

6-(N,N-Dimethylhydrazino)-9H-(2'-β-C-methyl-β-D-ribofuranosyl)purine (S1-12). The title compound was prepared from S1-2 and N,N-dimethylhydrazine as described for S1-4 (colorless oil, 42% for two steps). $^1$H NMR ($CD_3OD$): δ8.56 (s, 1H), 8.27 (s, 1H), 6.10 (s, 1H), 4.23 (d, 1H, J=9.0 Hz), 4.07 (m, 1H), 4.02 (d, 1H, J=2.1 Hz), 3.87 (dd, 1H, J=12.6, 3.3 Hz), 2.68 (s, 6H), 0.92 (s, 3H); MS: m/z 347 [M+Na]$^+$.

6-[$N^1$-(Hydroxyethyl)hydrazino]-9H-(2'-β-C-methyl-β-D-ribofuranosyl)purine (S1-13). A solution of 6-chloro-9H-(2'-β-C-methyl-2,3,5-tri-O-benzoyl-β-D-ribofuranosyl)adenine (S1-2) (449 mg, 0.73 mmol) in a mixture of ethanol (24 mL) and chloroform (12 mL) was treated with 2-hydroxyethylhydrazine (0.06 mL, 0.81 mmol). The reaction mixture was stirred at room temperature for 12 hours and concentrated. The residue was purified by flash chromatography on silica gel column using $CHCl_3$:MeOH (50:1–10:1) as eluents. The resulted product was treated with NaCN in MeOH followed by purification with flash chromatography on silica gel column using $CHCl_3$:MeOH (20:1 to 2:1) as eluents to afford 93 mg of compound S1-13 as a white solid (39% yield for 2 steps). $^1$H NMR ($CD_3OD$) δ 8.49 (1H, s), 8.23 (1H, s), 6.10 (1H, s), 4.26–4.19 (3H, m), 4.08–4.02 (2H, m), 3.92–3.84 (4H, m), 0.90 (3H, s). MS (EI) m/z 341 $(M+1)^+$.

6-[($N^2$-formyl)hydrazino]-9H-(2'-β-C-methyl-β-D-ribofuranosyl)purine (S1-14). Compound S1-14 was prepared from compound S1-3 (99.8 mg, 0.33 mmol) and formylhydrazine (24 mg, 0.40 mmol) in a mixture of ethanol (22 mL) and chloroform (6 mL). Purification of the crude product with flash chromatography on a silica gel column using $CHCl_3$:MeOH (20:1 to 2:1) as eluents afforded 4.7 mg of compound S1-14 as a white solid (4% yield). $^1$H NMR ($CD_3OD$) δ 8.63 (1H, s), 8.31 (1H, s), 6.13 (1H, s), 4.23 (1H, d, J=9.1 Hz), 4.09–4.02 (2H, m), 3.87 (1H, dd, J=2.8, 14.9 Hz), 0.92 (3H, s). MS (EI) m/z 323 $(M-1)^+$.

6-($N^1$-methylhydrazino)-9H-(2'-β-C-methyl-β-D-ribofuranosyl)purine (S1-15). Compound S1-15 was prepared as described above for S1-14 from compound S1-3 (160 mg, 0.53 mmol) and methylhydrazine (37 uL, 0.69 mmol) in a mixture of ethanol (18 mL) and chloroform (9 mL). Purification of the crude product with flash chromatography on a silica gel column using $CHCl_3$:MeOH (20:1 to 2:1) as eluents afforded 141 mg of compound S1-15 as a white solid (86% yield). $^1$H NMR ($CD_3OD$) δ 8.45 (1H, s), 8.17 (1H, s), 6.08 (1H, s), 4.20 (1H, d, J=8.8 Hz), 4.08–4.02 (2H, m), 3.87 (1H, dd, J=2.75, 12.4 Hz), 3.62 (3H, s), 0.88 (3H, s). MS (EI) m/z 311 $(M+1)^+$.

6-[N-Methoxycarbonyl)hydrazino)-9H-(2'-β-C-methyl-β-D-ribofuranosyl)purine (S1-16). The title compound was prepared from S1-2 and methylhydrazinocarboxylate as described for S1-4 (colorless oil, 55% for two steps). $^1$H NMR ($CD_3OD$): δ8.60 (s, 1H), 8.31 (s, 1H), 6.13 (s, 1H), 4.22 (d, 1H, J=8.7 Hz), 4.03 (m, 2H), 3.86 (m, 1H), 3.76 (s, 3H), 0.90 (s, 3H); MS: m/z 355 $[M+H]^+$.

6-[$N^2$-(Acetyl)hydrazino]-9H-(2'-β-C-methyl-β-D-ribofuranosyl)purine (S1-17). Compound S1-17 was prepared as described above for S1-13 from compound S1-2 (268 mg, 0.44 mmol) and acetic hydrazide (1.5 g, 20 mmol) in a mixture of ethanol (15 mL) and chloroform (7 mL). The crude was deprotected and purified by flash chromatography on a silica gel column using $CHCl_3$:MeOH, (20:1 to 2:1) as eluents to provide 26 mg of compound S1-17 as a white solid (18% yield for 2 steps). $^1$H NMR ($CD_3OD$) δ 8.75 (1H, s), 8.43 (1H, s), 6.25 (1H, s), 4.35 (1H, d, J=9.0 Hz), 4.21–4.14 (2H, m), 3.99 (1H, dd, J=2.59, 12.4 Hz), 2.22 (3H, s), 1.02 (3H, s). MS (EI) m/z 361 $(M+Na)^+$.

6-[$N^2$-Methylsulfonyl)hydrazino]-9H-(2'-β-C-methyl-β-D-ribofuranosyl)purine (S1-18). To a solution of S1-2 (880 mg, 1.44 mmol) in a mixture of ethanol (48 mL) and chloroform (24 mL) was added hydrazine (0.14 mL, 4.2 mmol) at 0° C. The reaction mixture was stirred at 0° C. to room temperature overnight. The reaction mixture was concentrated in vacuo, and the residue was purified by flash chromatography on a silica gel cloumn using $CHCl_3$:MeOH (50:1–10:1) as eluents to provide 503 mg of compound S1-18 as a tan solid (58%). Methyl sulfonyl chloride (0.18 mL, 2.3 mmol) was added to a solution of the resulted 6-(1-methyl)hydrozino compound (1.16 mg, 1.91 mmol) and triethyl amine (0.32 mL, 2.3 mmol) in methanol (12 mL) at −60° C. The reaction mixture was stirred overnight from −60° C. to room temperature. The reaction mixture was concentrated, and the crude product was purified by flash chromatography using $CHCl_3$:MeOH (50:1–10:1) as eluents to afford 510 mg of tan solid (39%). The resulted compound was deprotected with NaCN in methanol overnight at room temperature. Purification of the crude product by flash chromatography on a silica gel column using $CHCl_3$:MeOH (20:1–2:1) as eluents afforded 69 mg of product as a purple solid (25%). $^1$H NMR ($CD_3OD$) δ 8.63 (1H, s), 8.39 (1H, s), 6.13 (1H, s), 4.24 (1H, d, J=9.1 Hz), 4.10–4.01 (2H, m), 3.88 (1H, dd, J=2.75, 12.4 Hz), 3.07 (3H, s), 0.92 (3H, s). MS (EI) m/z 375 $(M+1)^+$.

6-Hydroxyamino-9H-(2'-β-C-methyl-β-D-ribofuranosyl)purine (S1-19). Compound S1-2 (105 mg, 0.17 mmol) was dissolved in hydroxyamine in water (50% wt, 2 mL), and the reaction mixture was heated at 80° C. for 4 h. After the reaction was completed, the solvent was removed in vacuo. The residue was purified by flash chromatography on a silica gel column using $CHCl_3$:MeOH (20:1–2:1) as eluents to provide 30 mg of the desired product in 58% yield. $^1$H NMR ($CD_3OD$) δ 8.58 (1H, s), 8.05 (1H, s), 6.09 (1H, s), 4.19 (1H, d, J=9.0 Hz), 4.08–3.99 (2H, m), 3.85 (1H, dd, J=2.59, 12.4 Hz), 0.93 (3H, s).

6-(N,O-Dimethylhydroxylamine)-9H-(2'-β-C-methyl-β-D-ribofuranosyl)purine (S1-20). The title compound was prepared from S1-2 and N,O-dimethylhydroxylamine as described for S1-4 (white solid, 89% for two steps). $^1$H NMR ($CD_3OD$): δ8.68 (s, 1H), 8.33 (s, 1H), 6.15 (s, 1H), 4.21 (d, 1H, J=9.0 Hz), 4.04 (m, 3H), 3.86 (s, 3H), 3.60 (s, 3H), 0.89 (s, 3H); MS: m/z 326 $[M+1]^+$.

6-(N-(t-Butyloxycarbonyl)aminoxy]-9H-(2'-β-C-methyl-β-D-ribofuranosyl)purine (S1-21). To a suspension of NaH (19.7 mg, 0.82 mmol) in THF (41 mL) and t-butyl-N-hydroxycarbamate (110 mg, 0.82 mmol) was added 6-chloro-9H-(2'-C-methyl-2,3,5-tri-O-benzoyl-β-D-ribofuranosyl)adenine (S1-2) (500 mg, 0.82 mmol) at 0° C. The reaction mixture was stirred for 30 minutes followed by removal of solvent in vacuo. Purification of the residue by flash chromatography on a silica gel column using $CHCl_3$:MeOH (20:1–2:1) as eluents afforded 340 mg of the protected product as a white solid (56%). Deprotection with NaCN in methanol and purification by flash chromatography ($CHCl_3$:MeOH, 20:1–2:1) afforded 25 mg of the desired product (17%). $^1$H NMR ($CD_3OD$) δ 8.90 (1H, s), 8.54 (1H, s), 6.22 (1H, s), 4.25 (1H, d, J=8.8 Hz), 4.12–4.02 (2H, m), 3.89 (1H, dd, J=2.47, 12.1), 1.50 (9H, s), 0.93 (3H, s); MS (EI) m/z 398 $(M+1)^+$.

6-[(N-Benzyloxycarbonyl)aminoxy]-9H-(2'-β-C-methyl-β-D-ribofuranosyl)purine (S1-22). To a suspension of NaH (3.8 mg, 0.16 mmol) in THF (8 mL) and N-(benzyloxycarbonyl)hydroxyamine (30 mg, 0.16 mmol) at 0° C. was added 6-chloro-9H-(2'-C-methyl-2,3,5-tri-O-benzoyl-β-D-ribofuranosyl)adenine (S1-2) (101 mg, 0.16 mmol). The reaction mixture was stirred for 30 minutes followed by removal of solvent in vacuo. Purification of the crude product by flash chromatography on a silica gel column using $CHCl_3$:MeOH (20:1–2:1) as eluents afforded 340 mg of the protected product as a white solid (56%). Deprotection with NaCN in methanol and purification by flash chromatography on a silica gel column using CHCl$_3$:MeOH (20:1–2:1) as eluents afforded 18 mg of the desired product (17%). $^1$H NMR (CD$_3$OD) δ 8.90 (1H, s), 8.50 (1H, s), 7.33 (5H, s), 6.22 (1H, s), 5.22 (2H, s), 4.24 (1H, d, J=9.0 Hz), 4.12–4.03 (2H, m), 3.88 (1H, dd, J=2.40, 12.0), 0.92 (3H, s); MS (EI) m/z 432 (M+1)$^+$.

N$^6$-(2-Aminoethyl)-9H-(2'-β-C-methyl-β-D-ribofuranosyl)adenine (S2-1). The compound was prepared from S1-2 and ethylenediamine as described for S1-4 (colorless oil, 45% for two steps). $^1$H NMR (CD$_3$OD): δ8.58 (s, 1H), 8.31 (s, 1H), 6.10 (s, 1H), 4.23 (d, 1H, J=9.0 Hz), 4.06 (m, 2H), 3.89 (m, 3H), 3.24 (t, 2H, J=5.7 Hz), 0.91 (s, 3H).

N,N'-Bis[N$^6$-9H-(2'-β-C-methyl-β-D-ribofuranosyl)adenin-6-yl]ethylenediamine (S2-2). The title compound was prepared from S1-2 and S2-1 as described for S1-4 (white solid, 35% for two steps). $^1$H NMR (DMSO-D$_6$): δ8.45 (s, 1H), 8.20 (s, 1H), 8.00 (s, 1H), 5.93 (s, 1H), 4.05 (d, 1H, J=9.0 Hz), 3.87 (m, 2H), 3.80 (m, 1H), 3.67 (m, 2H), 0.75 (s, 3H); MS: m/z 589 [M+H]$^+$.

Biological Activity of Exemplary Compounds

The following results are data obtained using the HCV replicon assay as described below, and the letters A, B, and C indicated EC$_{50}$ values of less than 10 μM, between 10 and 100 μM, and over 100 μM, respectively. The BVDV activity was shown as A, B, and C indicated EC$_{50}$ values of less than 25 μM, between 25–100 and over 100 μM.

HCV Replicon Assay

The replicon cells (Huh-7) contain replicating HCV replicon RNA, which was modified in the structural region (replacing the structural region with a neomycin resistance marker). Survival of the replicon cells under G418 selection relies on the replication of HCV RNA and subsequently expression of neomycin phosphoryltransferase. The ability of modified nucleoside libraries and compounds to suppress HCV RNA replication was determined using the Quantigene Assay Kit from Bayer. The assay measures the reduction of HCV RNA molecules in the treated cells. Replicon cells were incubated at 37° C. for 3 days in the presence of nucleoside libraries and compounds before harvested for detection. HCV subgenomic replicon cell line was provided by Dr. Bartenschlager. The assay protocol was modified based on literature procedure (V. Lohmann, F. Korner, J. O. Koch, U. Herian, L. Theilmann, R. Bartenschlager, *Science*, 1999, 285, 110–113).

Assay for Inhibition of BVDV

Bovine viral diarrhea virus (BVDV) (strain NADL) was provided by Dr. Ruben Donis and propagated in MDBK cells (ATCC). The nucleoside libraries and compounds were tested utilizing the modified protocol (V. B. Vassilev, M. S. Collett, R. O. Donis, *J. Viol.* 1997, 71, 471–478; S. G. Bagginski, D. C. Pevear, M. Seipel, S. C. C. Sun, C. A. Benetatos, S. K. Chunduru, C. M. Rice, M. S. Collett, *Proc. Natl. Acad. Sci. U.S.A.* 2000, 97, 7981–7986)

Results for Exemplary Compounds

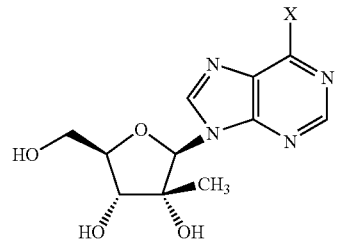

| Compound | 6-X | HCV Replicon EC$_{50}$ | BVDV, EC$_{50}$ |
|---|---|---|---|
| S1-4 | NHC$_6$H$_4$SCH$_3$-m | C | C |
| S1-5 | NHCH$_2$CHMePh | C | C |
| S1-6 | NHCH$_2$-tetrahydrofuranyl-2 | C | C |
| S1-7 | NHC$_6$H$_4$OCH$_2$CH$_3$-o | B | C |
| S1-8 | (see structure) | C | C |
| S1-9 | NHCH$_2$CH$_2$OH | B | C |
| S1-10 | N(CH$_2$CH$_2$OH)$_2$ | C | C |
| S1-11 | NHNH$_2$ | A | B |
| S1-12 | NHNMe$_2$ | A | A |
| S1-13 | NMeNH$_2$ | A | C |
| S1-14 | NHNHCHO | B | C |
| S1-15 | NHNHCOMe | A | C |
| S1-16 | NHNHCOOMe | A | B |
| S1-17 | N(NH$_2$)CH$_2$CH$_2$OH | A | A |
| S1-18 | NHNHSO$_2$Me | A | B |
| S1-19 | NHOH | A | B |
| S1-20 | N(Me)OCH$_3$ | B | C |
| S1-21 | ONHCOOC(CH$_3$)$_3$ | A | C |
| S1-22 | ONHCOOCH$_2$Ph | A | C |
| S1-23 | NHOMe | A | A |
| S2-1 | NHCH$_2$CH$_2$NH$_2$ | A | B |
| S2-2 | Dimer connector, see Scheme 2 | B | C |

It should be appreciated that numerous alternative assays may be performed to determine antiviral activity of contemplated compounds (data not shown), and exemplary additional assays may follow the general procedures as outlined below.

Hepatitis B Virus (HBV) Assay

The in vitro anti-HBV activity of nucleoside libraries and compounds was tested based on the reported protocol (W. E. Delaney, 4$^{th}$, R. Edwards, D. Colledge, T. Shaw, J. Torresi, T. G. Miller, H. C. Isom, C. T. Bock, M. P. Manns, C. Trautwein, S. Locarnini, *Antimicrob. Agents Chemother.*, 2001, 45, 1705–1713; W. E. Delaney, 4$^{th}$, T. G. Miller, H. C. Isom, *Antimicrob. Agents Chemother.*, 1999, 43, 2017–2026; B. E. Korba, J. L. Gerin, *Antiviral Res.*, 1992, 19, 55–70).

Human Immunodeficiency Virus (HIV) Assay

The in vitro HIV-1 activity of nucleoside libraries and compounds was tested utilizing the following modified protocol. Freshly isolated human PBMCs from healthy donors were infected with HIV-1 isolates for 3 hours. The cells were then washed three times to remove the viruses. The infected cells were plated into 96-well tissue culture plates and incubated for 7 days in the presence of serially diluted nucleoside analogues (with a medium change at day 4). A standardized HIV-1 p24 Elisa was performed to measure the extent of HIV replication in the presence of the compounds. (C. J. Petropoulos, N. T. Parkin, K. L. Limoli, Y. S. Lie, T. Wrin, W. Huang, H. Tian, D. Smith, G. A. Winslow, D. J. Capon, J. M. Whitcomb, *Antimicrob. Agents Chemother.*, 2000, 44, 920–928; Parkin, N. T., Y. S. Lie, N. Hellmann, M. Markowitz., S. Bonhoeffer, D. D. Ho, C. J. Petropoulos, *J. Infect. Disease*, 1999, 180, 865–870).

Human Rhinovirus (HRV) Assay

The in vitro activity of nucleoside libraries and compounds against HRV was tested based on the reported protocol (W.-M. Lee, W. Wang, R. Rueckert, *Virus Genes*, 1994, 9, 177–181; B. Sherry, R. Rueckert, *J. Virol.* 1985, 53, 137–143).

Respiratory Syncytial Virus (RSV) Assay

The RSV activity of nucleoside libraries and compounds was tested based on the reported protocol. Respiratory syncytial virus (strain A-2) was purchased from ATCC and virus stock was obtained by propagating the virus in Hep-2 cells. (P. R. Wyde, L. R. Meyerson, B. E. Gilbert, *Drug Dev. Res.* 1993, 28, 467–472).

Yellow Fever Virus (YFV) Assay

Yellow fever virus (vaccine strain 17-D) was purchased from ATCC (VR-1268) and the virus stock was obtained by infecting SW-13 cells from ATCC. The YFV activity of nucleoside libraries and compounds was tested utilizing the reported protocol (J. J. Schlesinger, S. Chapman, A. Nestorowicz, C. M. Rice, T. E. Ginocchio, T. J. Chambers, *J. Gen. Virol.* 1996, 77, 1277–1285).

Influenza Virus Assay

Influenza virus (type A, A/PR/8/34) was produced by infecting pathogen-free fertilized chicken eggs. The antiviral assay was performed on Madin Darby canine kidney (MDCK) cells from ATCC based on the reported protocol (E. H. Nasser, A. K. Judd, A. Sanchez, D. Anastasion, D. J. Bucher, *J. Virol.* 1996, 70, 8639–8644).

Thus, specific embodiments and applications of 2'-beta-methyl-6-substituted adenosine analogs and their use as antiviral agents have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A compound accordine to Formula 1

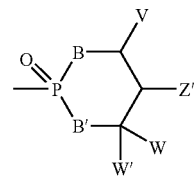

wherein Z is selected from the group consisting of alkyl, haloalkyl, hydroxyalkyl, O-alkyl, O-haloalkyl, O-hydroxyalkyl, alkenyl, haloalkenyl, hydroxyalkenyl, alkynyl, haloalkynyl, hydroxyalkynyl, and CN;

$R_3$ and $R_4$ are independently selected from the group consisting of H, alkyl, substituted alkyl, cycloalkyl, alkoxy, alkaryl, aryl, heteroaryl, substituted aryl, acyl, substituted acyl, and alkylsulfonyl; and R is selected from the group consisting of H,

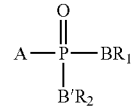  M1

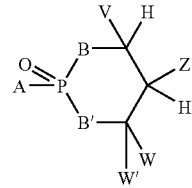  M2 wherein $BR_1$ and $B'R_2$ are independently selected from the group consisting of $OCH_2CH_2SC(=O)$t-butyl, $OCH_2OC(=O)$iPr, and NH-acyl, where acyl is an amino acid acyl group;

V, W, and W' are independently selected from the group consisting of hydrogen, alkyl, substituted alkyl, alkenyl, substituted alkenyl, alkynyl, substituted alkynyl, aryl, substituted aryl, alkaryl, and substituted alkaryl; and B and B' are independently O or NH; and Z' is hydrogen, CHWOH, CHWOCOW', SW, or $CH_2$aryl.

2. The compound of claim 1 wherein $R_3$ is H or $CH_3$, and wherein $R_4$ is selected from the group consisting of H, CHO, $C(O)CH_3$, $C(O)OCH_3$, $S(O)_2CH_3$, and $CH_3$.

3. The compound of claim 1 wherein V is m-chlorophenyl.

4. The compound of claim 2 wherein V is m-chlorophenyl.

5. The compound of claim 2 wherein R is H.

* * * * *

UNITED STATES PATENT AND TRADEMARK OFFICE
CERTIFICATE OF CORRECTION

PATENT NO. : 7,217,815 B2  Page 1 of 1
APPLICATION NO. : 10/530627
DATED : May 15, 2007
INVENTOR(S) : Haoyun An et al.

It is certified that error appears in the above-identified patent and that said Letters Patent is hereby corrected as shown below:

Column 28, lines 3-12, delete the structure and insert

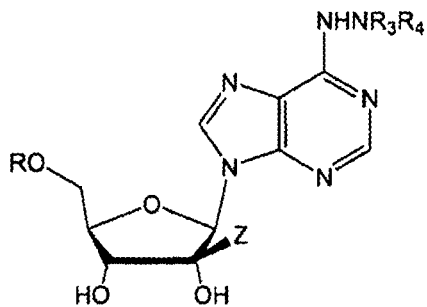

*Formula 1*

Column 28, lines 25-37, delete the two structures and insert

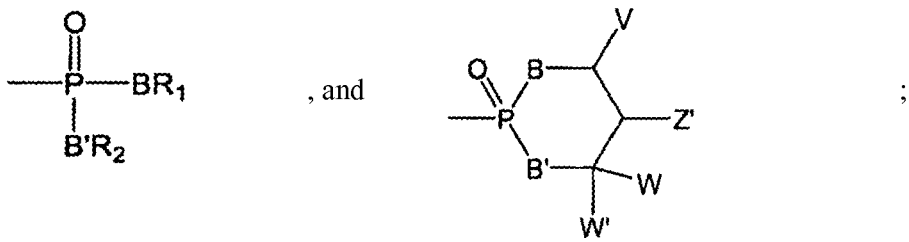

Signed and Sealed this

Twenty-fifth Day of March, 2008

JON W. DUDAS
*Director of the United States Patent and Trademark Office*